US006558522B1

(12) United States Patent
Williams et al.

(10) Patent No.: US 6,558,522 B1
(45) Date of Patent: May 6, 2003

(54) APPARATUS FOR ELECTROPHORESIS

(75) Inventors: Keith Leslie Williams, New South Wales (AU); Mark Molloy, New South Wales (AU); Andrew Arthur Gooley, New South Wales (AU); Nicolle Hannah Packer, New South Wales (AU); Ben Herbert, New South Wales (AU); Bradley Walsh, New South Wales (AU); George Fernwood, Larkspur, CA (US); David Garfin, Kensington, CA (US)

(73) Assignee: Macquarie Research Ltd., New South Wales (AU)

( * ) Notice: Subject to any disclaimer, the term of this patent is extended or adjusted under 35 U.S.C. 154(b) by 0 days.

(21) Appl. No.: 09/582,260

(22) PCT Filed: Dec. 22, 1998

(86) PCT No.: PCT/AU98/01066

§ 371 (c)(1),
(2), (4) Date: Sep. 14, 2000

(87) PCT Pub. No.: WO99/33550

PCT Pub. Date: Jul. 8, 1999

(30) Foreign Application Priority Data

Dec. 23, 1997 (AU) .............................................. PP1086

(51) Int. Cl.[7] ........................ B01D 57/02; B01D 59/42; B01D 59/50; B01D 61/42; B01D 61/58; C02F 1/469; C07K 1/28; C08F 2/58
(52) U.S. Cl. ..................................................... 204/459
(58) Field of Search .......................................... 204/459

(56) References Cited

U.S. PATENT DOCUMENTS

| 4,151,065 A | | 4/1979 | Kaplan et al. |
| 4,305,799 A | * | 12/1981 | Schwarz et al. ............. 204/455 |
| 5,116,483 A | | 5/1992 | Lander |
| 5,609,743 A | | 3/1997 | Sasagawa et al. ........... 204/600 |
| 5,637,203 A | | 6/1997 | Sarrine ........................ 204/616 |
| 5,750,015 A | | 5/1998 | Soane et al. ................. 204/454 |
| 5,773,645 A | | 6/1998 | Hochstrasser ............... 204/456 |
| 5,989,400 A | * | 11/1999 | Islam ........................... 204/466 |
| 6,113,766 A | * | 9/2000 | Steiner et al. ............... 204/606 |

FOREIGN PATENT DOCUMENTS

| EP | 0 457 526 A2 | 5/1991 |
| GB | 2 284 494 | 6/1995 |

* cited by examiner

Primary Examiner—Jill Warden
Assistant Examiner—Jennine Brown
(74) Attorney, Agent, or Firm—Morgan, Lewis & Bockius LLP

(57) ABSTRACT

An electrophoresis apparatus for the simultaneous electrophoretic separation of a plurality of component mixtures using a disposable tray having a plurality of parallel troughs shaped to retain an elongate strip of isoelectric focusing medium and sufficient liquid to immerse the elongate strip. A frame is provided to retain the tray in a horizontal position using a pair of rotatably mounted support members moving between an open and closed position. Support members are also connected to a plurality of electrodes aligned with each of the troughs so that the electrodes are positioned clear of the troughs in the open position and positioned in the troughs when in the closed position.

11 Claims, 6 Drawing Sheets

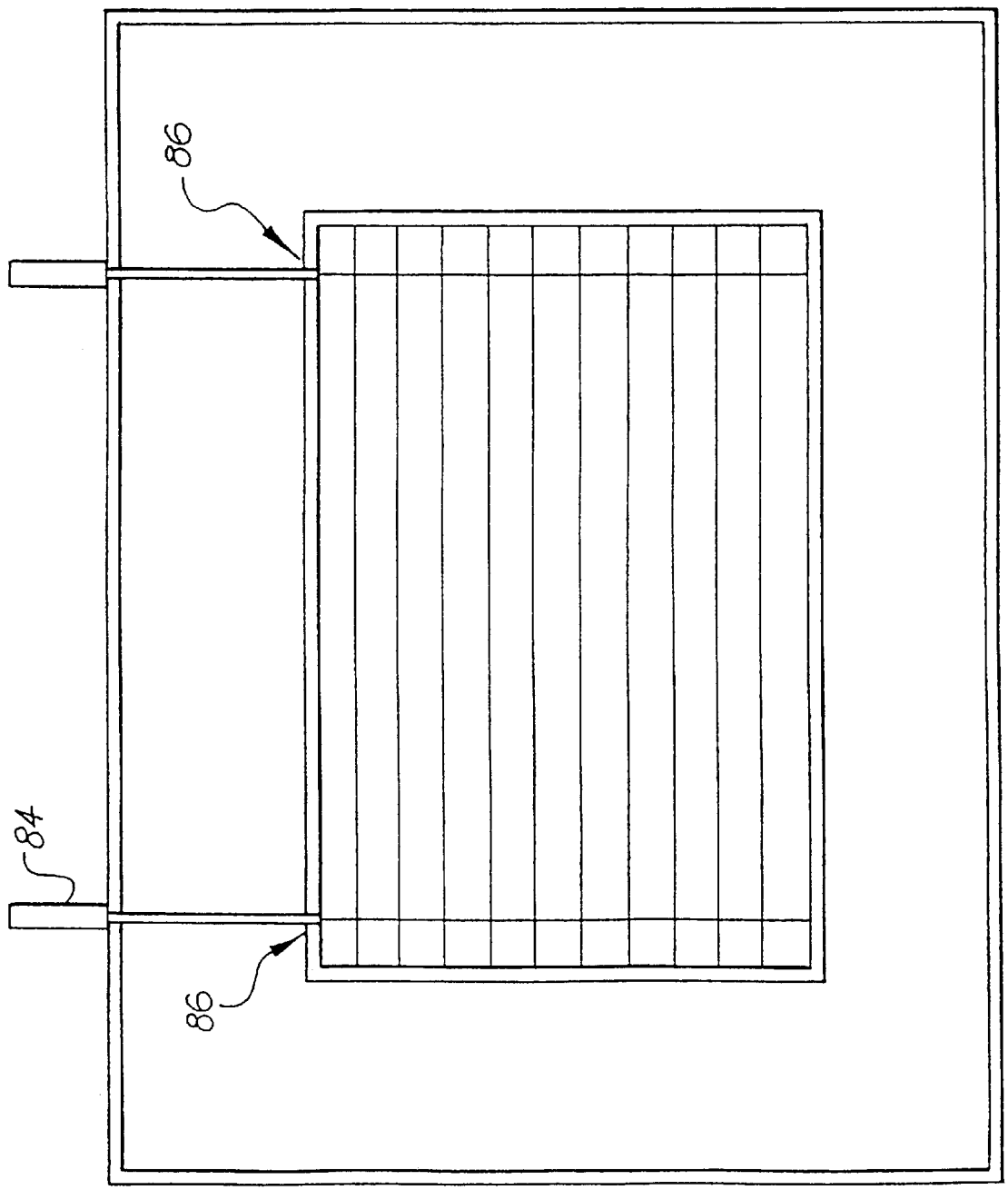

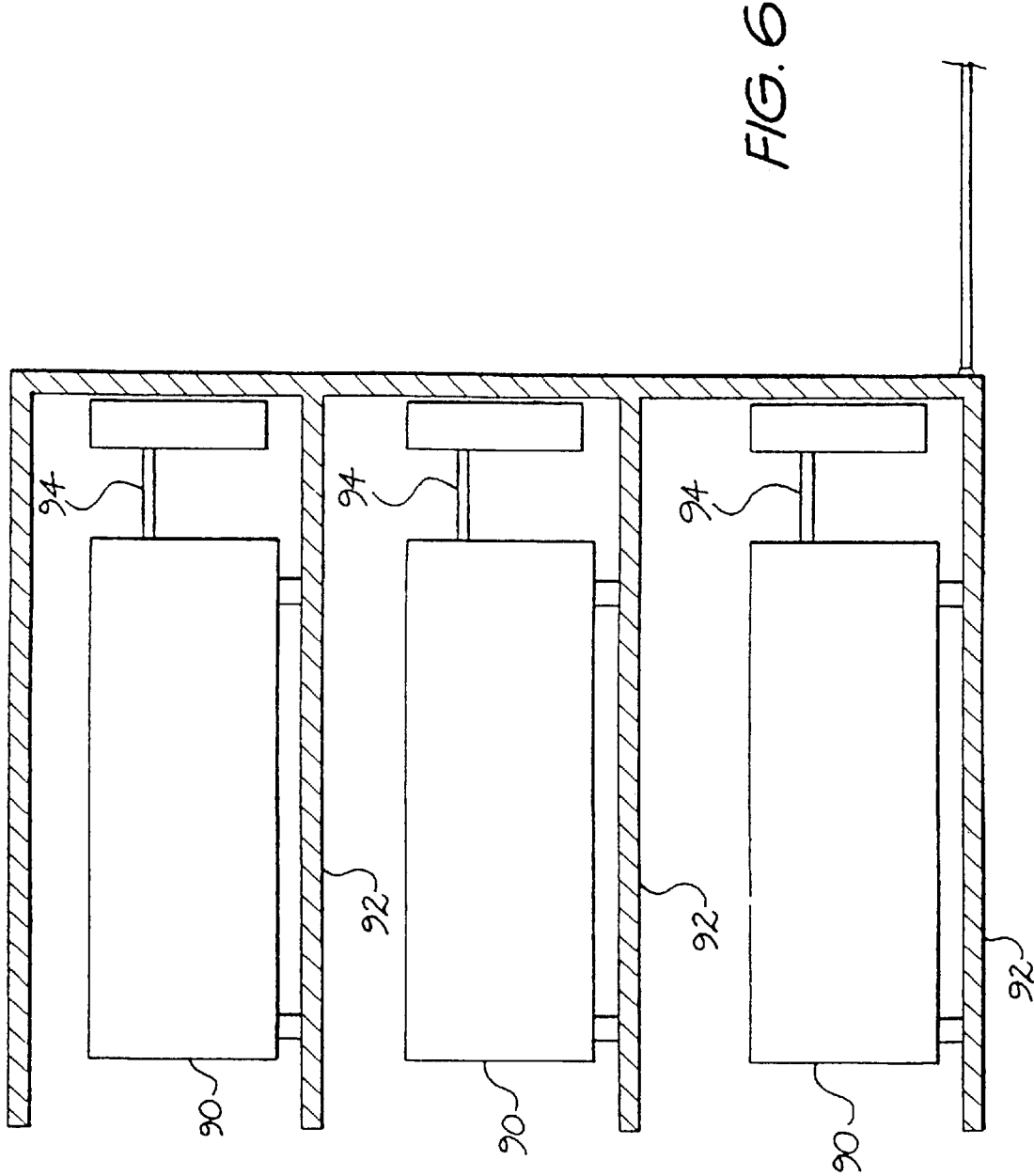

APPARATUS FOR ELECTROPHORESIS

TECHNICAL FIELD

The invention relates to apparatus for the separation of macromolecules by electrophoresis, particularly by isoelectric focusing.

BACKGROUND ART

Two-dimensional (2D) electrophoresis is a useful and well-known separation technique for purifying macromolecules and separating complex macromolecule mixtures, often providing a much higher resolving power than typical electrophoretic separation in one dimension or direction.

In two-dimensional electrophoresis, separation is performed under two different conditions or according to two different separation parameters, one in a first direction and the other in a second direction which is usually perpendicular to the first. The first dimension of the separation is typically performed in an elongate rod-shaped or strip-shaped gel with migration and separation of macromolecules occurring along the length of the gel. Once the macromolecules have been grouped into individual zones along the length of the gel, the gel is placed along one edge of a slab gel and the electric current is imposed across the both gels in a direction perpendicular or otherwise transverse to the first (elongate) gel. This causes the migration of the macromolecules from each zone of the elongate gel into the slab gel, and the separation of macromolecules within each zone.

A variety of combinations can be used for the first and second dimension separations. Separation based on charge or pI can be followed by separation based on molecular weight, for example. Likewise, separation in a gel of one concentration can be followed by separation in a gel of the same material but of another concentration. Two-dimensional separations have also been used to create a stepwise change in pH to separate first in a homogeneous gel and then in a pore-gradient gel, to separate in media containing first one protein solubiliser and then another, or in media containing a protein solubiliser first at one concentration and then at another concentration, to separate first in a discontinuous buffer system and then in a continuous buffer system, and to separate first by isoelectric focusing and then by homogeneous or pore gradient electrophoresis. Combinations such as these can be used to separate many kinds of macromolecules, including serum or cell proteins, bacterial proteins, non-histone chromatin proteins, ribosomal proteins, mixtures of ribonucleo-proteins and ribosomal proteins, glycoproteins, and nucleic acids.

There are many difficulties and disadvantages with existing apparatus suitable for running immobilised pH gradients (IPGs). There is no possibility of rehydrating the IPGs in the apparatus. All commercially available systems have electrodes which are removable and therefore can be placed incorrectly in use. Many of the electrodes are resilient which can result in poor electrical contact. Due the size and configuration of the apparatus available, they require a relatively large quantity of paraffin oil (~250 mL). This not only results in the expense of discarding the oil but also requires intense washing between runs and after each use. Due the inherent design of current systems they have a relatively large footprint and thus require a large amount of bench space in use.

Another disadvantage of two-dimensional electrophoresis systems is that they are labor-intensive and time-consuming. Elongate gels are awkward to handle and their use is prone to error and loss of samples and time. The present inventors have now developed a new electrophoresis apparatus that is useful for running IPGs.

DISCLOSURE OF INVENTION

In a first aspect, the present invention consists in an electrophoresis apparatus for the simultaneous electrophoretic separation of a plurality of component mixtures, the apparatus comprising:

a tray which is detachable from and removable from the apparatus, the tray defining a plurality of troughs, each trough being shaped to retain an elongate strip of isoelectric focusing medium and sufficient liquid to immerse the elongate strip;

a frame to retain the tray in a predetermined position;

a pair of electrodes adapted to be positioned at or near each end of the tray, wherein the electrodes are arranged such that each electrode is aligned with each of the plurality of troughs at the respective ends of the tray; and electrically conductive connection means for connecting to a means for imposing an electric potential between the electrodes.

In one preferred form, the tray is provided with the electrodes positioned in the troughs and having electrical terminals positioned at one end of the leads. When the tray is placed in the frame, the terminals connect to plugs positioned therein thus allowing the imposing of an electric potential between the leads.

A principal advantage of the present invention is that it allows the tray to be disposable although trays could be provided for multiple use, if desired. In the case of disposable trays containing electrodes any suitable conductive material compatible with electrophoresis could be used as the electrode although clearly cheaper electrodes such s graphite would be preferable to platinum if the tray is to be thrown away after use.

Preferably, the tray is fabricated of a heat-transmissive material to permit temperature control of the troughs through the tray. In one form, the tray comprises 3 to 24, preferably 6 to 18, substantially parallel troughs. The troughs are preferably of equal length and each from 6 cm to 20 cm in length. It will be appreciated, however, that the tray may have any number of troughs, and the troughs be any suitable length and depth.

The apparatus according to the first aspect of the present invention also allows the possibility to stack a plurality of trays and carry out multiple separations simultaneously. The trays are removable for loading etc, and then would simply plug in to a suitable frame adapted to receive a number of trays stacked horizontally. Thus one power supply could be used for a number of trays.

Alternatively, several apparatus containing the frame with the tray attached may be stacked to carry out simultaneous separations.

In use, each elongate strip of isoelectric focusing medium placed in a trough will be subjected to the electric potential.

The electrically conductive connecting means may be electrical leads attachable to the electrodes for connecting the electrodes to a suitable power source.

In a related aspect, the present invention consists in an electrophoresis apparatus for the simultaneous electrophoretic separation of a plurality of component mixtures, the apparatus comprising:

a detachable tray containing a plurality of troughs, each trough shaped to retain an elongate strip of isoelectric focusing medium and sufficient liquid to immerse the elongate strip:

a frame to retain the tray in a substantially horizontal position;

a pair of support members rotatably mounted to the frame such that when the tray is retained therein each support member spans the plurality of troughs, each the support member supporting a plurality of electrodes arranged such that one electrode from each support member is aligned with each of the plurality of troughs;

means for rotating each support member between a first position in which all electrodes thereon extend into the troughs and a second position in which all electrodes thereon are clear of the troughs; and electrically conductive connection means for connecting to a means for imposing an electric potential between the electrodes on one support member and the electrodes on the other support member.

Preferably, each of the support members has an axis of rotation that is transverse to the parallel troughs. The apparatus may further include a means for biasing each the support member into the first position. The support members, in addition to being rotatably mounted to the frame, may also be movably mounted thereto at a variable distance from each other.

Preferably, the tray is fabricated of a heat-transmissive material to permit temperature control of the troughs through the tray. In one form, the tray comprises 3 to 24, preferably 6 to 18, substantially parallel troughs. The troughs are preferably of equal length and each from 6 cm to 20 cm in length.

The electrically conductive connecting means may be electrical leads attachable to the electrodes for connecting the electrodes to a suitable power source.

In a third aspect, the present invention consists in a method of separating a macromolecule comprising subjecting the macromolecule to electrophoresis in an apparatus according to the first or second aspects of the present invention.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

In order that the present invention may be more clearly understood, preferred forms will be described with reference to the following examples and accompanying drawings.

BRIEF DESCRIPTION OF THE DRAWINGS

FIG. 5 is a schematic of an apparatus in accordance with the first aspect of the present invention assembled; and FIG. 6 is a cross section view of a yet further variant of the present invention being a multi-apparatus containing three electrophoresis apparatus stacked vertically.

MODES FOR CARRYING OUT THE INVENTION

Figure 1:
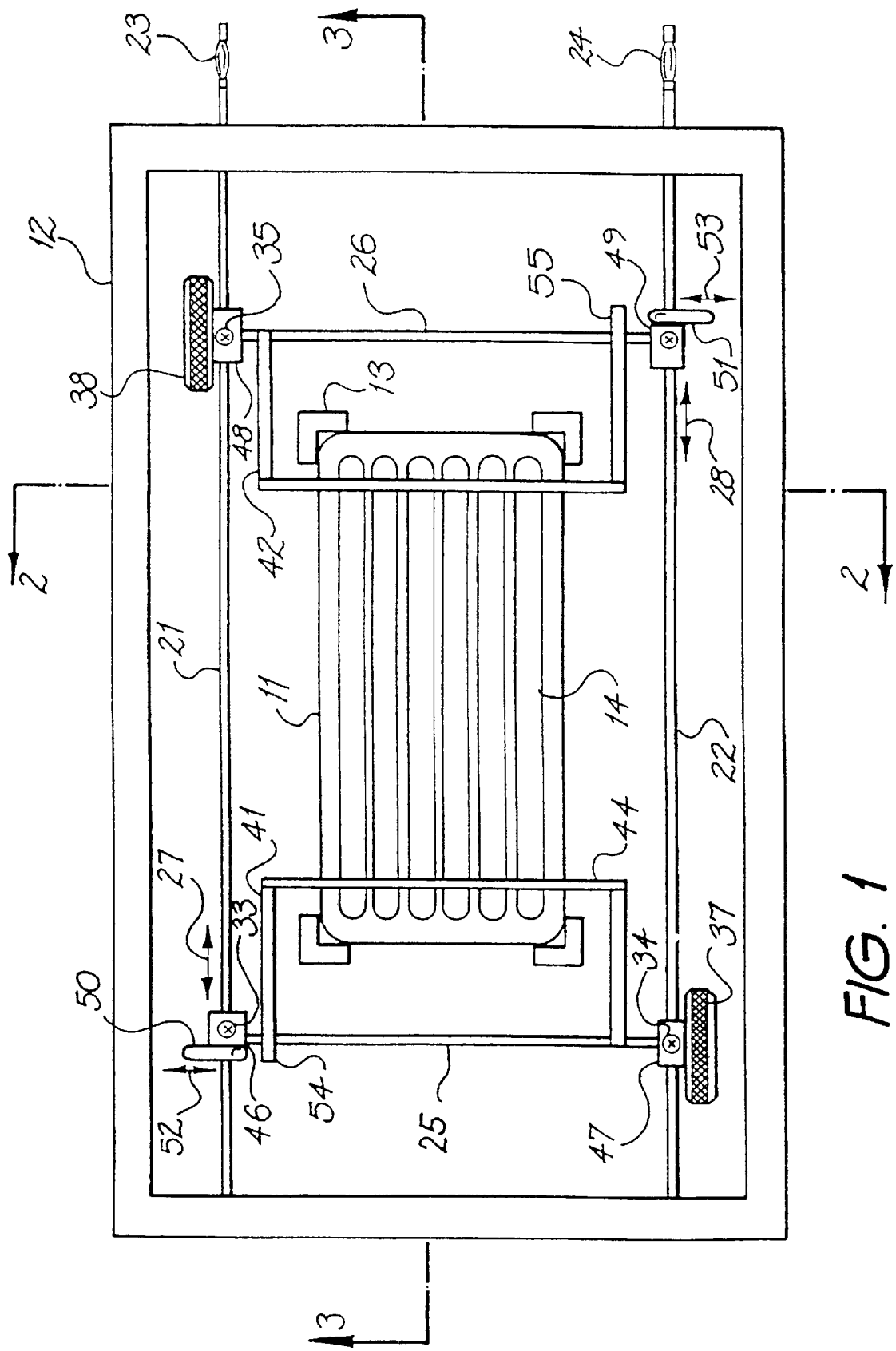
FIG. 1 is a top plan view of an apparatus in accordance with an embodiment of the present invention.

While the invention is susceptible to a wide range of configurations, procedures, and embodiments, it will best be understood by a detailed examination of one specific structure and its mode of operation. Such a structure is shown in the drawings, and its construction and use are explained below.

Figure 2:
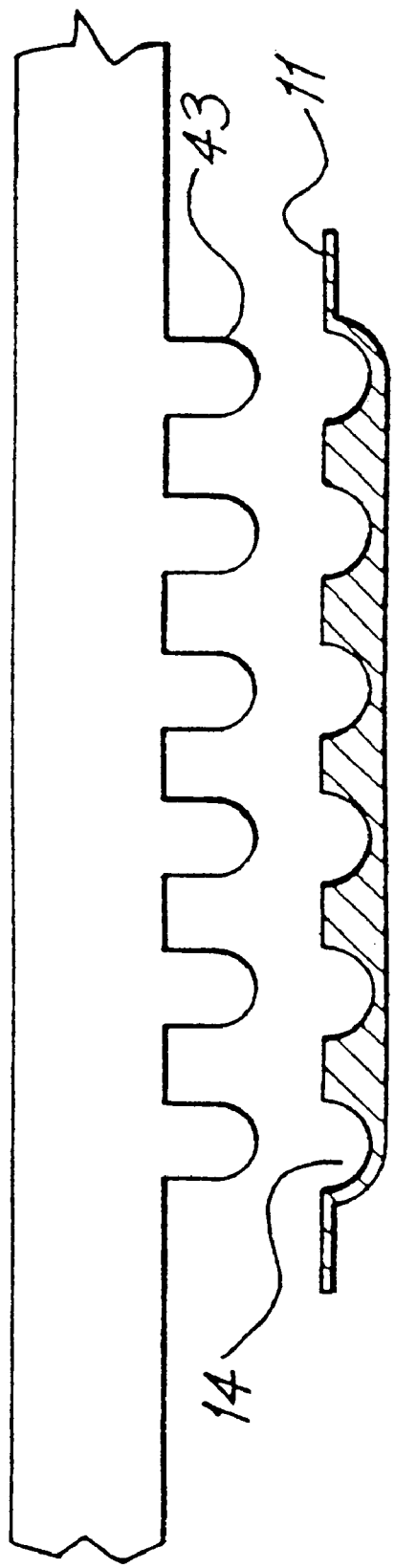
FIG. 2 is a transverse cross section of the tray and one electric lead array of the apparatus of FIG. 1, taken along the line 2—2 of FIG. 1.

In the top plan view of FIG. 1, the tray 11 is shown, held inside a frame 12 by retaining blocks 13. The tray is shown in transverse cross section in FIG. 2, and contains an array of parallel troughs 14, which are visible from above in FIG. 1 and in profile in FIG. 2. Each trough extends almost the entire length of the tray 11, and is long enough to contain a single rod- or strip-shaped gel that will be used as the first dimension separation in two-dimensional electrophoresis. The length is otherwise not critical and can vary to accommodate gel strips or rods of various sizes. An appropriate length for most applications of this invention will generally range from about 6 cm to about 20 cm. The troughs will generally be of equal length. The depth, width, spacing, and profile of each trough is also not critical and can vary. An appropriate depth for most applications will generally range from about 0.3 cm to about 3.0 cm, and appropriate width likewise from about 0.3 cm to about 3.0 cm, and appropriate center-to-center spacing from about 0.5 cm to about 3.5 cm. While a curved profile is shown in FIG. 2, other profiles such as a rectangular profile can also be used. Finally, the tray depicted in the drawings contains six troughs, but the invention extends to trays with any plurality of troughs. For most applications, the appropriate number of troughs will range from 3 to 24, and preferably from 6 to 18.

In certain embodiments of the invention, the tray 11 is designed as a disposable item intended for a single use. Preferably, the tray also selves as a heat-transfer element to allow temperature control of the gel strips and liquids that are placed in the troughs. The tray can thus, for example, be a thermoformed plastic component whose walls are thin enough to permit heat transfer to and from each trough to a temperature control device such as a heating element or heat sink contacting the underside of the tray. The temperature control device, although not shown in the drawings, can be incorporated into the structure of the frame 12.

Figure 3:
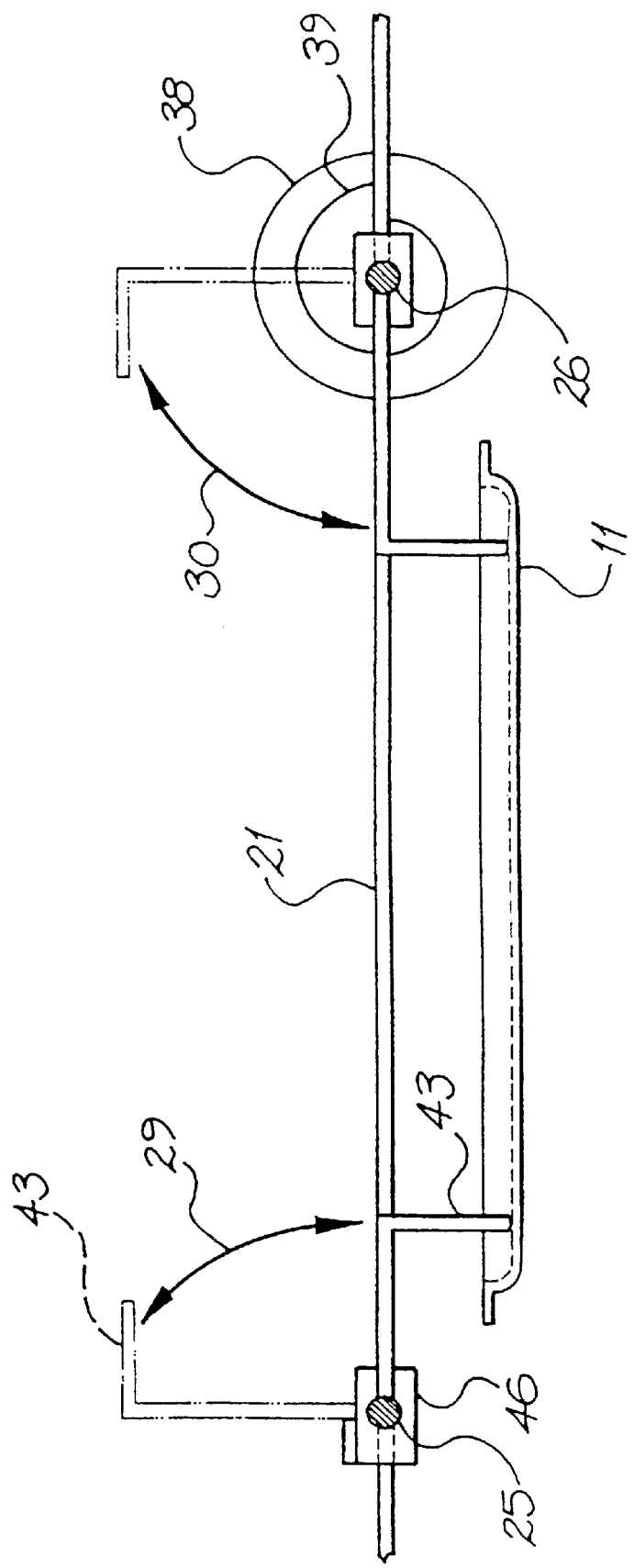
FIG. 3 is a longitudinal cross section of the tray and electric lead support portions of the apparatus of FIG. 1, taken along the line 3–5 of FIG. 1.

Also mounted to the frame 12 are pair of rails 21, 22, spanning the length of the frame interior and running parallel to each other and to the troughs of the tray 11. Each rail is electrically conductive and is electrically connected to banana plugs 23, 24 or other electrical connectors on the frame exterior. A pair of transverse support members 25, 26 are mounted across the two rails 21, 22 in both a longitudinally slidable and axially rotatable manner. Each support member is longitudinally and independently slidable in the directions of the arrows 27, 28 of FIG. 1, and is rotatable about its axis in the directions of the arrows 29, 30 shown in FIG. 3. Set screws 33, 34, 35, 36 can be tightened to fix the support members in any selected location along the rails 21, 22 without inhibiting the axial rotation of the support members 25, 26. Rotation of each support member is facilitated by knobs 37, 38 for manual rotation by the operator. Each support member is also equipped with a spring (one of which 39 is shown in FIG. 3) to bias the support member toward the inward position.

Attached to each rotatable support member is a smaller frame 41, 42, each of these smaller frames rotating with the rotation of its respective support member. Extending from each of these smaller frames is a series of electrodes 43 (the electrodes of one frame are visible in FIG. 2) in an array corresponding to the troughs 14 of the tray 11. When the tray 11 is in place in the outer frame 12 and the smaller frames 41, 42 are rotated inward such that electrodes 43 are lowered, the electrodes are aligned with the troughs. The widths of the electrodes and the spacings between them are selected so that one lead will extend into each trough and contact the gel or IPG strip contained in that trough. The electrodes 43 and the support bar 44 from which they extend can thus be shaped like the teeth of a comb.

To impose an electric potential across the lengths of gel strips contained in the troughs, each of the two arrays of electrodes is separately supplied by one of the two exterior plugs 23, 24. This can be accomplished in any of various ways. In the arrangement shown in the drawings, the rails 21, 22, the rotatable support arms 25, 26, the smaller frames 41, 42, and the electrodes 43 (the teeth of the comb) are all electrically conductive. The sliding blocks 46, 47, 48, 49 that join the rotatable support arms 25, 26 to the rails 21, 22 are non-conductors. Affixed to two of the sliding blocks 33, 36 are movable fittings 50, 51 that are of electrically conductive material. Each of these fittings is slidable in the direction indicated by the arrows 52, 53. When slid inward (transverse to the rails, and toward the centre axis of the frame), the fittings contact both the rails 21, 22 and protruding members 54, 55 of the smaller frame, thereby forming an electrical connection between each rail and one of the smaller frames.

The construction shown in these drawings and described above can be modified in various ways. For example, external electric leads can be attached directly to the rotatable support arms 25, 26 rather than the rails 21, 22, and the rails may be made of nonconductive material. The rotation of the rotatable support arms 25, 26 is shown in FIG. 3, where the solid lines show the support arms and electrodes in a lowered position with the electrodes extending into the troughs, and the dashed lines show the support arms and electrodes in a raised position where the electrodes 43 are clear of the troughs. An alternative to this arrangement is one in which the axis of rotation of the rotatable support arms 25, 26 passes through one end of each bar and is perpendicular to the bar itself. A vertical axis of rotation is also contemplated. Biasing of the electrodes into the troughs to insure proper and uniform electrical contact is as described above achieved by spring loading the rotatable arms. An alternative to the use of springs or similar devices is the use a gravitational force by using a biased weight distribution in the rotatable arm.

Although not shown in these drawings, the smaller frames 41, 42 to which the electrodes are mounted can also support sample receptacles, one aligned with each trough to supply sample mixtures to the troughs. The apparatus can also contain a lid or cover to protect the gels and liquids contained in the troughs and to prevent operator contact with exposed electric leads. Furthermore, the tray 11 can be inserted into the outer frame from above or slid into position by side entry into the outer frame. Still further, the retaining blocks 13 can be replaced by any structure affixed to the outer frame or any shape of the frame that will accomplish a similar purpose of stabilising the position of the tray relative to the rotatable support arms. Still further, the troughs can contain removable pins or other barriers to ensure proper positioning of the gels, particularly when the gels are shorter than the troughs.

Other structural variations will be readily apparent to those skilled in the design, construction and use of electrophoretic apparatus.

While the apparatus of this invention can be used for any type of gel strip, the invention is particularly useful for gels with immobilised functional groups distributed along its length for isoelectric focusing. The immobilised groups form a pH gradient by virtue of a charge distribution already present in the groups or the capability of being charged to form a pH gradient. Alternatively, the pH gradient can be formed by carrier ampholytes that are not immobilised in the strip matrix.

Strips containing immobilised groups are known among electrophoresis practitioners and are commercially available. The strips are commonly termed "IPG" (immobilised pH gradient) strips, and examples are disclosed in U.S. Pat. No. 4,130,470 (Rosengren et al., issued Dec. 19, 1978), the contents of which are incorporated herein by reference. The matrix may be a solid support material such as a granule or fibrous, or membrane material, or it may be a gel. Examples of matrix materials are polyacrylamide, cellulose, agarose, dextran, polyvinylalcohol, starch, silicon gel, acryloyl amino ethoxyl ethanol (AAEE), and polymers of styrene divinyl benzene, as well as combinations of these materials.

Examples of positively charged or chargeable groups are amino groups and other nitrogen containing groups. Examples of negatively charged or chargeable groups are carboxylic acid groups, sulphonic acid groups, boronic acid groups, and phosphonic or phosphoric acid groups, as well as esters of these acids. Other examples will be readily apparent to those skilled in the art. Immobilisation of the groups on the matrix can be achieved by covalent bonding or any other means that will secure the positions of the groups and prevent their migration under the influence of an electric field or due to the movement of fluids or solutes through the matrix. A preferred means of incorporating charged groups into a polymeric gel matrix is by copolymerising charged monomers or charged crossing agents with the gel monomers. The concentration of the groups will preferably vary in a monotonically increasing or decreasing manner to form an immobilised pH gradient suitable for isoelectric focusing.

IPG strips that are made of gels often contain a backing to secure the dimensional integrity of the gel. The backing is generally fluid-impermeable and electrically nonconductive. The IPG strip is generally supplied in dry form and requires rehydration prior to use. This is conveniently achieved by placing the strip in contact with the sample solution which serves as the rehydrating agent. Rehydration can be performed in the apparatus of this invention in the troughs themselves, while the electrical electrodes are raised above the troughs. IPG strips with backing are best rehydrated with the gel side facing down (i.e., the backing facing Up). The troughs of the tray are preferably sufficiently deep that each IPG strip can be rehydrated with a different sample solution without risking cross contamination from adjacent sample solutions. Once rehydrated, the strips can be separated from the trays and stored frozen until ready for use.

Once the IPG strip is rehydrated and equilibrated to the temperature at which electrophoresis is to occur, the strip is preferably turned over to expose its gel side for contact with the electrodes. The need to turn the strips over can be eliminated by providing an auxiliary means for electrical contact between the gel and the electrode, recognising that the electric potential will not extend through the backing. One means of achieving this is to provide each strip with a hole at each end and to place a wick, in the form of a piece of soft paper or similar absorbent material soaked with a conductive liquid, on top of the strip over the hole. The hole in the strip will fill with conductive liquid, and the wick will ensure electrical contact between the electrode and the liquid occupying the hole (and hence the gel on the underside of the strip).

Prior to electrophoresis, the remaining space in the troughs above the gel strips can be filled with paraffin oil or a similar electrically non-conductive liquid, to prevent the evaporation of moisture from the gel during electrophoresis. Once the electrodes are in place, the electric potential is applied to the leads, and each solute migrates to a position along the length of the gel where the gel pH is equal to the isoelectric point of the solute. Once the solutes are separated in this the electric potential is removed, and the support arms supporting the electrodes are rotated away from the troughs. The tray is then removed from the frame, the protective paraffin oil is poured out, and the gel strips are removed from the troughs. Alternatively, the gel strips can be equilibrated in the troughs for the second stage of the two-dimensional separation.

Figure 4:
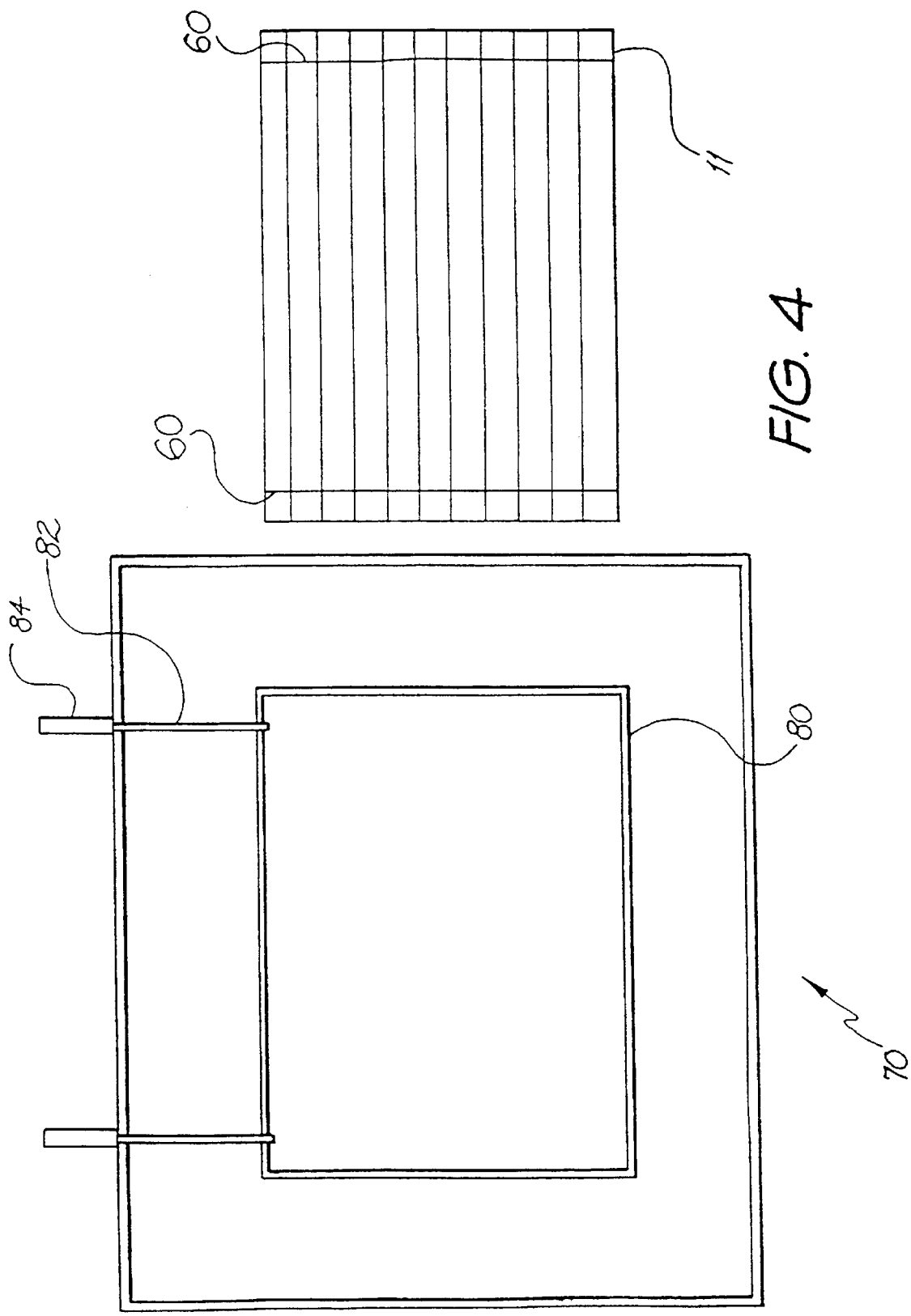
FIG. 4 is a schematic of an apparatus in accordance with the first aspect of the present invention dis-assembled.

FIG. 4 shows a variant of the invention in which permanent electrodes 60 are incorporated in the disposable tray 11. The apparatus generally indicated at 70 includes a frame or holder 80 for receiving the tray 11 and the electrode connections 82 connect to the electrodes 60 at contact points 86 as is best seen in FIG. 5. The electrode connections are connected to plugs 84 for connection to a power supply.

FIG. 5 shows a yet further embodiment in which the apparatus provides a stack of cells 90 supported on frames 92 one above the other. Each cell 90 is removable from the stack for loading and simply plugs into an electrode connection 94 allowing a single power supply to be used for a number of units.

The apparatus of this invention lends itself well to automation, with such actions as the insertion of the tray, the addition of the paraffin oil, the lowering of the electrodes, the imposition of the electric potential for a preselected period of time, the raising of the electrodes, and the release of the tray, all controlled by a programmed sequence.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An electrophoresis apparatus for the simultaneous electrophoretic separation of a plurality of component mixtures, the apparatus comprising:

a tray which is detachable from and removable from the apparatus, the tray defining a plurality of troughs, each trough being shaped to retain an elongate strip of isoelectric focusing medium and sufficient liquid to immerse the elongate strip;

a frame to retain the tray in a predetermined position;

a pair of support members adapted to be positioned at or near each end of the tray, each support member supporting a plurality of depending electrodes arranged such that each electrode is aligned with and locates in each trough of the tray when the tray is in the predetermined position, the electrodes being located near the respective ends of the tray; and electrically conductive connection means for connecting to a means for imposing an electric potential between the electrodes on one support member and the electrodes on the other support member.

2. An electrophoresis apparatus as claimed in claim 1 characterised in that the tray is provided with the electrodes positioned in the troughs and having electrical terminals positioned at one end of the leads whereby when the tray is placed in the frame, the terminals connect to plugs positioned therein thus allowing the imposing of an electric potential between the leads.

3. An electrophoresis apparatus as claimed in claim 1 characterised in that the tray is fabricated of a heat-transmissive material to permit temperature control of the troughs through the tray.

4. An electrophoresis apparatus as claimed in claim 1 characterised in that the tray comprises 6 to 18, substantially parallel troughs.

5. An electrophoresis apparatus as claimed in claim 1 characterised in that the troughs are of substantially equal length and from 6 cm to 20 cm in length.

6. An electrophoresis apparatus for the simultaneous electrophoretic separation of a plurality of component mixtures, the apparatus comprising:

a detachable tray containing a plurality of substantially parallel troughs, each trough shaped to retain an elongate strip of isoelectric focusing medium and sufficient liquid to immerse the elongate strip;

a frame to retain the tray in a substantially horizontal position;

a pair of support bars adapted to be positioned at or near each end of the tray, each support bar supporting a plurality of depending electrodes arranged such that when the support bar is in a first position, each electrode is aligned with and locates in each trough of the tray when the tray is in the predetermined position, the electrodes being located near the respective ends of the tray, wherein each support bar is rotatably mounted to the frame via a support member such that when the tray is retained therein each support member spans the plurality of troughs; and wherein means are provided for rotating each support member between the first position in which all electrodes thereon extend into the troughs and a second position in which all electrodes thereon are clear of the troughs.

7. An electrophoresis apparatus as claimed in claim 6 characterised in that each of the support members has an axis of rotation that is transverse to the parallel troughs.

8. An electrophoresis apparatus as claimed in claim 7 characterised in that the apparatus further includes a means for biasing each support member into the first position.

9. An electrophoresis apparatus as claimed in claim 6 characterised in that the support members, are rotatably mounted to the frame, and are also movably mounted thereto at a variable distance from each other.

10. An electrophoresis apparatus as claimed in claim 6 characterised in that, the tray is fabricated of a heat-transmissive material to permit temperature control of the troughs through the tray.

11. An electrophoresis apparatus as claimed in claim 6 characterised in that the tray comprises 6 to 18, troughs which are of substantially equal length and from 6 cm to 20 cm in length.

* * * * *